(12) United States Patent
Partain et al.

(10) Patent No.: US 8,483,803 B2
(45) Date of Patent: Jul. 9, 2013

(54) SYSTEMS AND METHODS FOR TRACKING AND TARGETING OBJECT IN A PATIENT USING IMAGING TECHNIQUES

(75) Inventors: Larry Partain, Los Altos, CA (US); Hassan Mostafavi, Los Altos, CA (US); Stavros Prionas, Menlo Park, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 779 days.

(21) Appl. No.: 12/210,813

(22) Filed: Sep. 15, 2008

(65) Prior Publication Data

US 2010/0069742 A1 Mar. 18, 2010

(51) Int. Cl.
*A61B 6/00* (2006.01)

(52) U.S. Cl.
USPC ........... 600/427; 600/425; 600/407; 600/431; 382/128

(58) Field of Classification Search
USPC ........................................................ 382/128
See application file for complete search history.

(56) References Cited

U.S. PATENT DOCUMENTS

| | | | |
|---|---|---|---|
| 6,480,565 B1 | 11/2002 | Ning | |
| 6,987,831 B2 | 1/2006 | Ning | |
| 2004/0081273 A1 | 4/2004 | Ning | |
| 2006/0023840 A1* | 2/2006 | Boese | ......................... 378/98.12 |
| 2006/0094950 A1 | 5/2006 | Ning | |
| 2006/0182326 A1* | 8/2006 | Schildkraut et al. | ........... 382/132 |
| 2007/0127804 A1* | 6/2007 | Yoshida et al. | ................ 382/131 |

* cited by examiner

*Primary Examiner* — Long V. Le
*Assistant Examiner* — Farshad Negarestan
(74) *Attorney, Agent, or Firm* — Vista IP Law Group, LLP

(57) ABSTRACT

A method for use in a medical procedure includes obtaining a contrast-enhanced image of a portion of a patient, the portion of the patient having an object, obtaining a non-contrast-enhanced image of the portion, wherein the contrast-enhanced image and the non-contrast-enhanced image are created at different times, and determining a position of the object using the contrast-enhanced image and the non-contrast-enhanced image. A method for use in a medical procedure includes obtaining a contrast-enhanced image of a portion of a patient, the portion of the patient having an object, obtaining a non-contrast-enhanced image of the portion, and determining a position of the object using the contrast-enhanced image and the non-contrast-enhanced image, wherein the act of determining the position is performed is substantially real time.

67 Claims, 9 Drawing Sheets

← 400

| Feature | With Iodine (HU) | | Without Iodine (HU) | | Δ Iodine (HU) |
|---|---|---|---|---|---|
| | Mean | Std Dev | Mean | Std Dev | |
| IDC | 101.0 | 43.9 | 47.0 | 38.1 | 54.0 |
| Glandular | 49.6 | 33.8 | 25.3 | 41.9 | 24.3 |
| Contrast Δ Mean (HU) | 51.4 | Noise | 21.7 | Noise | |
| Adipose | -109.5 | 32.5 | -91.1 | 29.0 | 18.4 |

FIG. 4

SYSTEMS AND METHODS FOR TRACKING AND TARGETING OBJECT IN A PATIENT USING IMAGING TECHNIQUES

FIELD

This invention relates to systems and methods for tracking and targeting object in a patient using imaging techniques.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Sometimes during a radiation therapy, the patient may undergo movement, such as, breathing motion. In such cases, it may be desirable to determine positions of a moving target such that a radiation beam may be adjusted accordingly to treat the target. Existing techniques for determining a position of an object requires imaging of the object. However, in some cases, the object that is desired to be tracked may not be discernable from the images. This is especially the case when the target that is desired to be tracked is a small cancerous region embedded in some healthy tissue, such as the glandular breast tissue.

SUMMARY

In accordance with some embodiments, a method for use in a medical procedure includes obtaining a contrast-enhanced image of a portion of a patient, the portion of the patient having an object, obtaining a non-contrast-enhanced image of the portion, wherein the contrast-enhanced image and the non-contrast-enhanced image are created in different times, and determining a position of the object using the contrast-enhanced image and the non-contrast-enhanced image.

In accordance with other embodiments, a system for use in a medical procedure includes a processor configured for obtaining a contrast-enhanced image of a portion of a patient, the portion of the patient having an object, obtaining a non-contrast-enhanced image of the portion, wherein the contrast-enhanced image and the non-contrast-enhanced image are created at different times, and determining a position of the object using the contrast-enhanced image and the non-contrast-enhanced image.

In accordance with other embodiments, a computer product having a medium that stores a set of instructions, an execution of which causes a process to be performed, the process includes obtaining a contrast-enhanced image of a portion of a patient, the portion of the patient having an object, obtaining a non-contrast-enhanced image of the portion, wherein the contrast-enhanced image and the non-contrast-enhanced image are created at different times, and determining a position of the object using the contrast-enhanced image and the non-contrast-enhanced image.

In accordance with other embodiments, a method for use in a medical procedure includes obtaining a contrast-enhanced image of a portion of a patient, the portion of the patient having an object, obtaining a non-contrast-enhanced image of the portion, and determining a position of the object using the contrast-enhanced image and the non-contrast-enhanced image, wherein the act of determining the position is performed is substantially real time.

In accordance with other embodiments, a system for use in a medical procedure includes a processor configured for obtaining a contrast-enhanced image of a portion of a patient, the portion of the patient having an object, obtaining a non-contrast-enhanced image of the portion, and determining a position of the object using the contrast-enhanced image and the non-contrast-enhanced image, wherein the act of determining the position is performed is substantially real time.

In accordance with other embodiments, a computer product having a medium that stores a set of instruction, an execution of which causes a process to be performed, the process includes obtaining a contrast-enhanced image of a portion of a patient, the portion of the patient having an object, obtaining a non-contrast-enhanced image of the portion, and determining a position of the object using the contrast-enhanced image and the non-contrast-enhanced image, wherein the act of determining the position is performed is substantially real time.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 4 illustrates a table summarizing examples of Hounsfield Units for different types of tissues in contrast-enhanced image and non-contrast-enhanced image in accordance with some embodiments;

DESCRIPTION OF THE EMBODIMENTS

Figure 1:
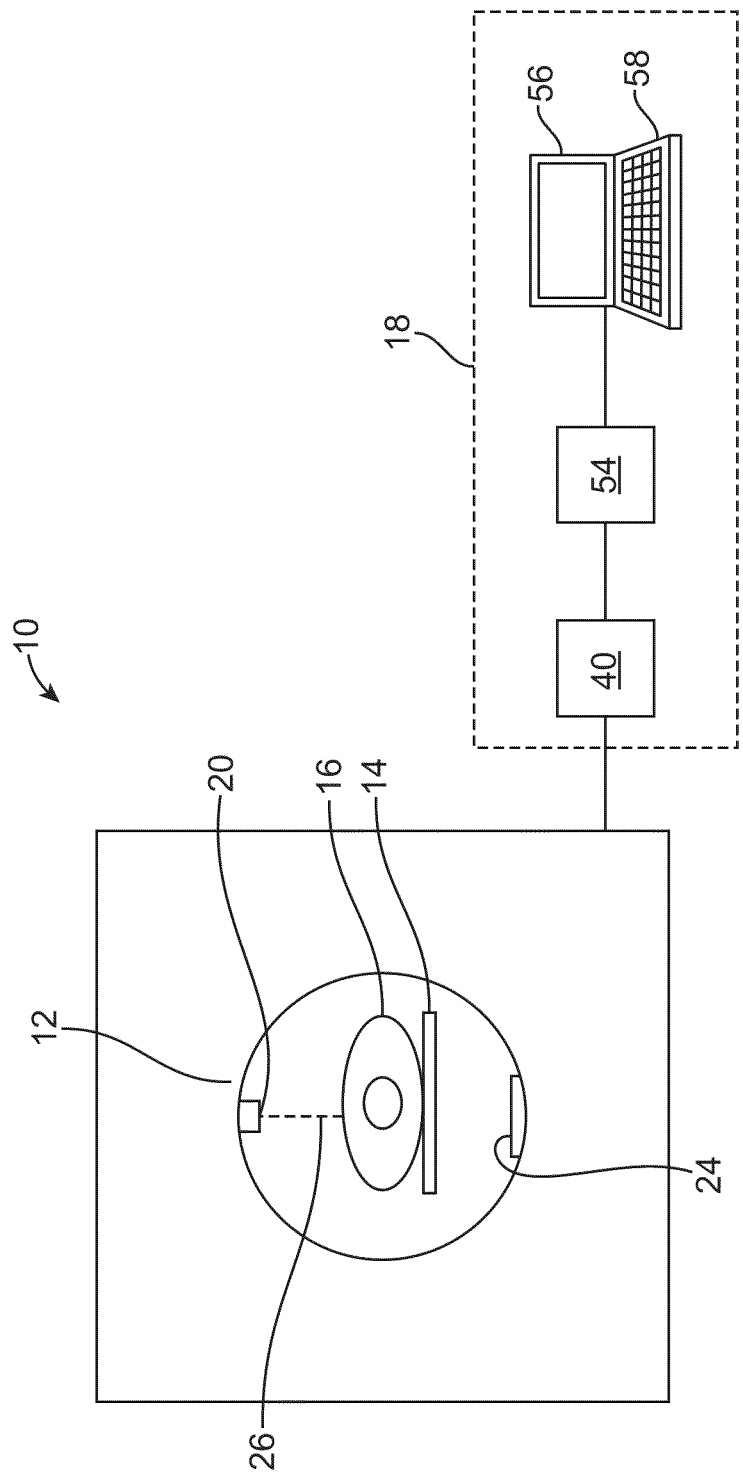
FIG. 1 illustrates a radiation system with which embodiments described herein may be practiced.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a computed tomography (CT) image acquisition system 10 for providing images in accordance with some embodiments. The system 10 includes a gantry 12, and a panel 14 for supporting a patient 16. The gantry 12 includes a x-ray source assembly 20 that projects a beam 26 of x-rays, such as a fan beam or a cone beam (CB), towards a detector assembly 24 on an opposite side of the gantry 12 while a portion of the patient 16 is positioned between the x-ray source assembly 20 and the detector assembly 24. In the illustrated embodiment, the x-ray source assembly 20 is configured to deliver radiation suitable for imaging, and the detector assembly 24 is configured to generate image data in response to radiation incident on the detector assembly 24. The detector assembly 24 has a plurality of sensor elements configured for sensing a x-ray that passes through the patient 16. Each sensor element generates an electrical signal representative of an intensity change of the x-ray beam as it passes through the patient 16.

In the illustrated embodiment, the CT image system 10 also includes a processor 54, a monitor 56 for displaying data, and an input device 58, such as a keyboard or a mouse, for inputting data. The processor 54 is coupled to a control 40. The rotation of the gantry 12 and the operation of the x-ray source assembly 20 are controlled by the control 40, which provides power and timing signals to the x-ray source assembly 20 and controls a rotational speed and position of the gantry 12 based on signals received from the processor 54. The control 40 also controls an operation of the detector assembly 24. For example, the control 40 can control a timing of when image signal/data are read out from the detector assembly 24, and/or a manner (e.g., by rows or columns) in which image signal/data are read out from the detector assembly 24. Although the control 40 is shown as a separate component from the gantry 12 and the processor 54, in alternative embodiments, the control 40 can be a part of the gantry 12 or the processor 54.

During a scan to acquire x-ray projection data (i.e., CT image data), the x-ray source assembly 20 projects a beam 26 of x-rays towards the detector assembly 24 on an opposite side of the gantry 12, while the gantry 12 rotates about the patient 16. In one embodiment, the gantry 12 makes a 360° rotation around the patient 16 during image data acquisition. Alternatively, if a full cone detector (e.g., detector centered with the beam) is used, the system 10 may acquire data while the gantry 12 rotates 180° plus the angle of the beam pattern. Other angles of rotation may also be used, depending on the particular system being employed. In one embodiment, the detector assembly 24 is configured to generate at least 900 frames of images in less than 1 second. In such case, the gantry 12 only needs to rotate around the patient 16 once in order to collect sufficient amount of image data for reconstruction of computed tomography images. In other embodiments, the detector 24 may be configured to generate frames at other speeds.

It should be noted that the system 10 is not limited to the configuration described above, and that the system 10 may have other configurations in other embodiments. For example, in other embodiments, the system 10 may have a different shape. In some embodiments, the gantry 12 may include an arm, in which cases, the radiation source 20 may be coupled to the arm, and is located outside the bore of the system 10. In other embodiments, the radiation source 20 of the system 10 may have different ranges of motions and/or degrees of freedom. For example, in other embodiments, the radiation source 20 may be rotatable about the patient 16 completely through a 360° range, or partially through a range that is less than 360°. Also, in other embodiments, the radiation source 20 is translatable relative to the patient 16. Further, the radiation source 20 is not limited to delivering diagnostic energy in the form of x-ray, and may deliver treatment energy for treating a patient. In such cases, the x-ray source assembly 20 may include a collimator for adjusting a shape of the x-ray beam. In some embodiments, the collimator includes one or more leaves (not shown) for creating radiation with certain prescribed characteristics. In further embodiments, the system 10 may include a separate treatment source for delivering treatment radiation. The treatment source may be located next to the source 20, or may be located at 90° apart from the source 20.

Figure 2:
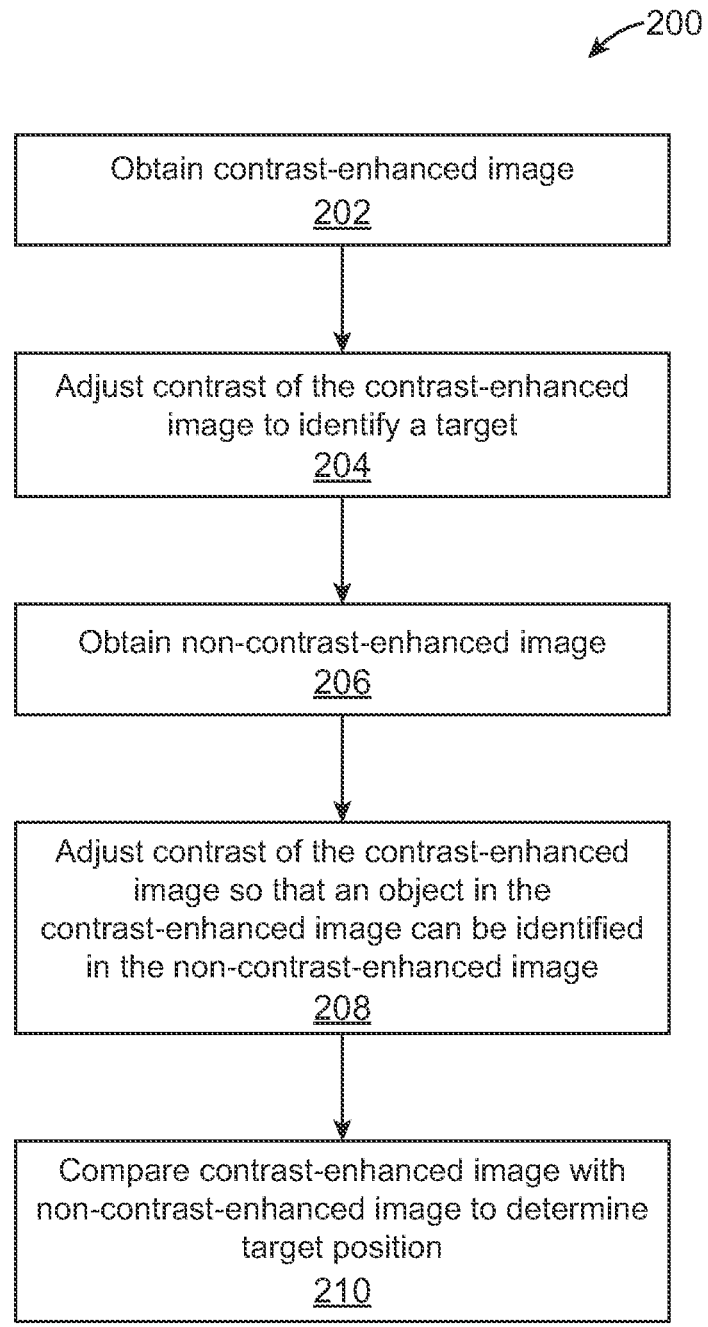
FIG. 2 illustrates a method for determining a target position in accordance with some embodiments.

FIG. 2 illustrates a method 200 for determining a position of a target using the system 10 in accordance with some embodiments. First, a contrast-enhanced image is obtained (Step 202). As used in this specification, the term "contrast-enhanced image" refers to an image that is generated for a portion of a patient that includes a contrast agent. In the illustrated embodiments, the contrast-enhanced image was previously created (e.g., as in a previous day or previous imaging session), and the act of obtaining the contrast-enhanced image is performed by the processor 54 receiving or retrieving the previously created contrast-enhanced image, e.g., from a storage medium. Alternatively, the contrast-enhanced image may be created in the same day or in the same session in which the rest of the steps of method 200 are performed. Also, in other embodiments, the act of obtaining the contrast-enhanced image may also include the act of creating the contrast-enhanced image, as described herein.

Various techniques may be used to create a contrast-enhanced image. In the illustrated embodiments, a contrast agent is introduced inside the patient's 16 body, and more specifically, into a vascular system of the patient 16. For example, the contrast agent can be administered with a mechanical power injector via an intravenous catheter that is placed in antecubital or forearm vein, at a rate between 2 to 6 milliliter (mL) per second. In the illustrated embodiments, about 50 to 70 mL of contrast agent is administered to the patient 16. However, other amounts of contrast agent can be introduced inside the patient's body, depending on a patient's size, the size of a region inside a patient that is desired to be imaged, and/or a requirement of a particular procedure.

A variety of contrast agent can be administered to the patient 16. In the illustrated embodiment, the contrast agent includes iodine, which has a k-absorption edge (K-edge) of 33 keV. Alternatively, gadolinium (Gd) (having a k-edge of 50.2 keV) chelated with diethylenetriaminepentaa-cetic acid (DTPA) can be used. Gd-DTPA is well tolerated by humans, and no serious side effects have been reported. The contrast agent can also include materials, such as holmium (having a k-edge of 56 keV), erbium (having a k-edge of 58 keV), lanthanum, cerium, praseodymium, neodymium, samarium, europium, terbium, dysprosium, thulium, ytterbium, lutetium (having a k-edge of 63.3 keV), and other rare earth elements. Compounds, DTPA complexes, ethylenediamine tetraacetic acid (EDTA) complexes, nitrilotriacetic acid (NTA) complexes, and other chelate compounds, formed from any of the above mentioned elements can also be used. Elements with atomic numbers higher than that of gadolinium is particularly suitable for the contrast agent because x-ray absorption of body tissue would be lower at higher x-ray photon energies. However, elements with atomic numbers lower than that of gadolinium can also be used, depending on a particular k-edge requirement of an application. K-edge energies for various materials are known. Other soluble, non-toxic, chelate compounds can also be used. In addition, noble gases such as Xenon, and agents composed of stable isotopes of radio nuclides such as Ti, Yb, Cs, Xe, I, In, and Tc. It should be noted that other contrast agents may also be used in different embodiments, and therefore, the method 200 should not be limited to the examples of agent described herein.

After the contrast agent is injected into the patient, the system 10 is then used to generate a contrast-enhanced image. In the illustrated embodiments, the x-ray source assembly 20 projects a beam 26 of x-rays towards the detector assembly 24 on an opposite side of the gantry 12, while the gantry 12 rotates about the portion in the patient 16 that has the injected contrast agent. As the gantry 12 rotates, the detector assembly 24 generates a sequence of projection images at different gantry angles. Because the projection images include images of the portion of the patient 16 that has injected contrast agent, any of the projection images may be considered a contrast-enhanced image. In some cases, a number of projection images may be used in a reconstruction process to create a three-dimensional image (CT image), in which case, the CT image itself, or any part of the CT image (such as a two-dimensional slice), may also be considered a contrast-enhanced image.

Figure 3A:
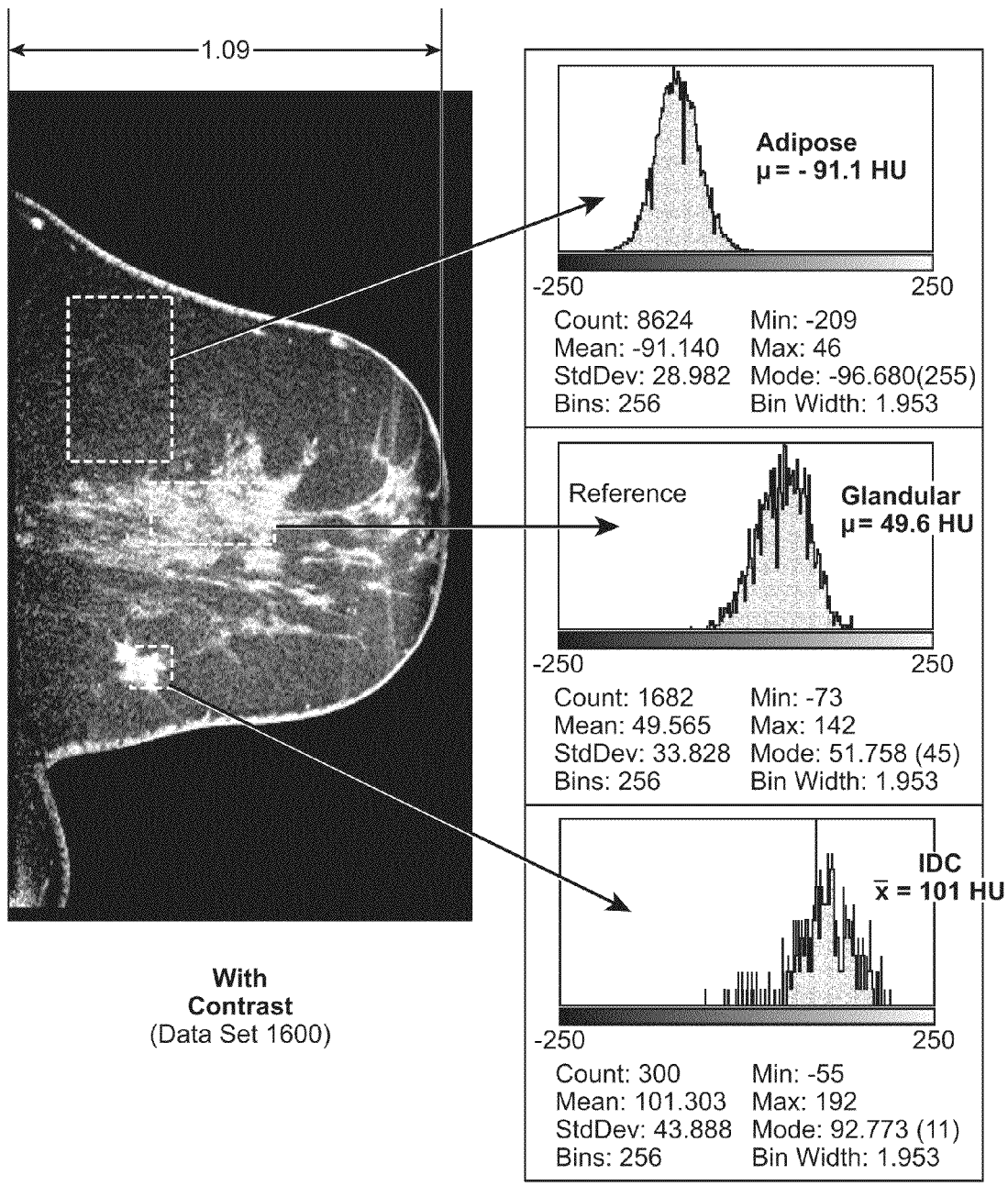
FIG. 3A illustrates an example of a contrast-enhanced image.
Figure 3B:
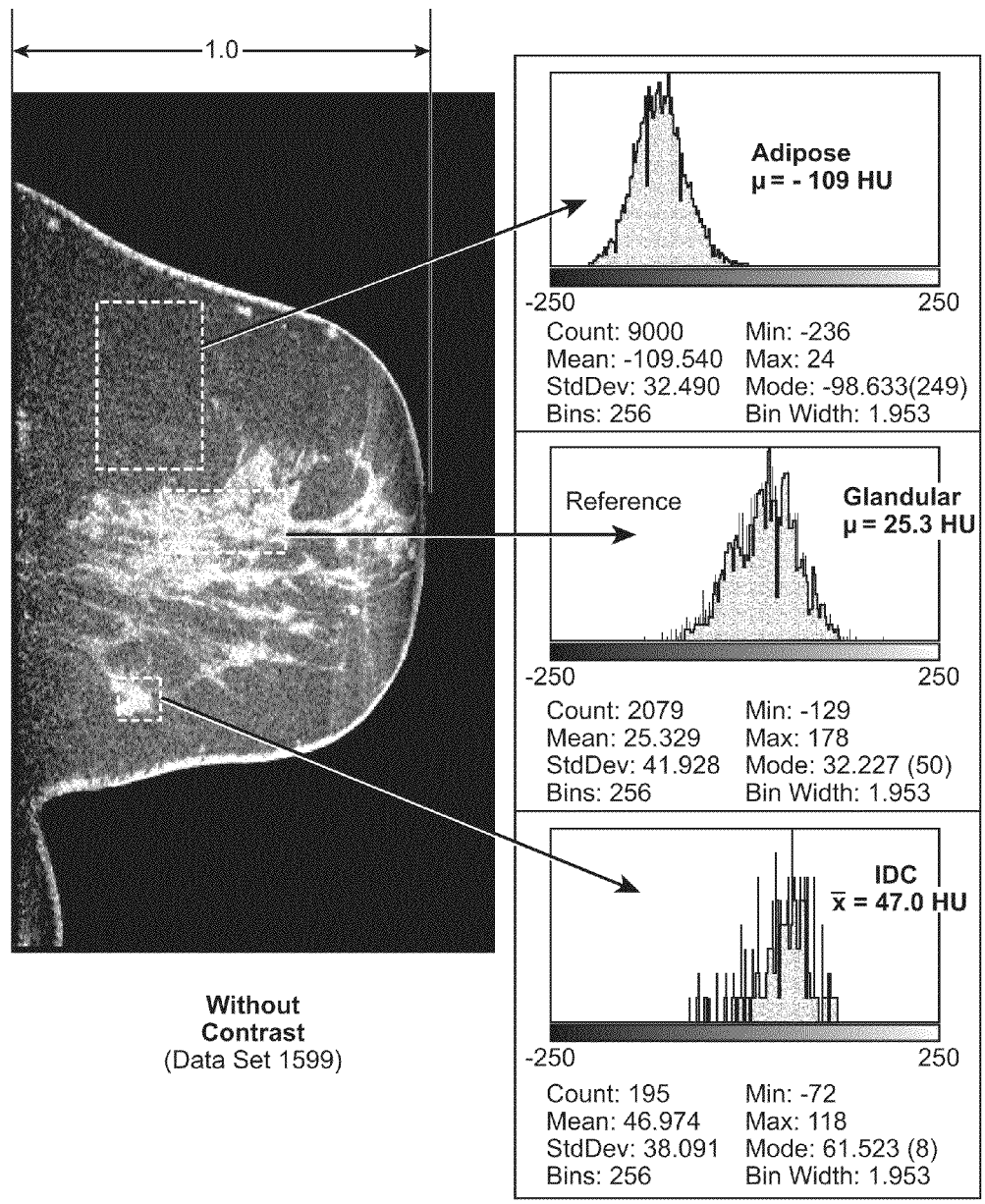
FIG. 3B illustrates an example of a non-contrast-enhanced image.

After the contrast-enhanced image is obtained, the contrast-enhanced image may be adjusted to identify a target (Step 204). In the illustrated embodiments, the contrast and/or brightness of the display of the contrast-enhanced image is adjusted such that only images of objects with Hounsfield Unit (HU) above a certain prescribed threshold (i.e. brightness), and/or within a certain prescribed HU range (i.e. contrast), are visible. For example, in some embodiments, the HU threshold (or brightness) adjustment may be to approximately 100 HU, with a range (or contrast) adjustment to approximately 33 HU (i.e. from 100 HU to 133 HU). Such technique allows object(s) that may potentially be cancerous tissue to be identified from the contrast-enhanced image. For the case in which the portion of the patient 16 that is being imaged is the breast, the contrast-enhanced image may include image of adipose (or fat), image of glandular, and image of invasive ductal carcinoma (IDC). FIG. 3A illustrates an example of such contrast-enhanced image. As shown in the figure, in the contrast-enhanced image, adipose has corresponding average HU that is approximately −91, the glandular has corresponding average HU that is approximately 49.6, and IDC has corresponding average HU that is approximately 101. Thus, by adjusting the brightness and contrast in the contrast-enhanced image so that only object(s) with HU that is within a prescribed HU range is displayed, possible suspects of IDC may be identified. For comparison, FIG. 3B illustrates an example of a non-contrast-enhanced image of the same region of the patient 16 as that in FIG. 3A. As used in this specification, the term "non-contrast-enhanced image" refers to any image for a portion of a patient that does not include a contrast agent. As shown in the figure, in the non-contrast-enhanced image, adipose has corresponding average HU that is approximately −109, the glandular has corresponding average HU that is approximately 25.3, and IDC has corresponding average HU that is approximately 47.

FIG. 4 illustrates a table 400 that summarizes the values in the example described above. The table 400 also indicates the standard deviations of the HU statistics for various objects—i.e., IDC, glandular, and adipose, in both the contrast-enhanced image and the non-contrast-enhanced image. As shown in the table 400, the measurable image contrast difference (between the means of the IDC and glandular) is the large value 51.4 HU in the contrast-enhanced image, but only 21.7 HU in the non-contrast-enhanced image. The standard deviations of the HU statistics in the regions of interest (ROIs) for the IDC and glandular are in the 33 to 44 HU range, all smaller than the 51.4 HU "image contrast" with the enhancement, but all larger than the 21.7 HU in the non-contrast-enhanced image. Standard deviation is a statistical measurement of the variation of HU values about their means and it is one numerical metric of the noise contained in the ROI. Image contrast is relatively more visible and identifiable when it is larger than "noise." However this identification becomes very difficult, if not impossible, when image contrast becomes less than the noise. Also, the standard deviation (noise) of the adipose tissue ROI is given in the last row of table 400, to show that it is of the same order of magnitude as those for IDC and glandular. Thus, the "noise" of the image is less than the difference between the glandular and malignant IDC tissue in the contrast-enhanced image but not in the non-contrast image. Further, the last column of table 400 shows that the addition of contrast agent increased the mean ROI values of adipose and glandular regions by 18 and 24 HU, respectively, in the non-contrast-enhanced image. However, this increase in the IDC was about twice as big (namely 54 HU) in the contrast-enhanced image, which is what made the IDC stand out in the contrast-enhanced image. In the above examples, the healthy tissue. (e.g., glandular tissue) of the patient 16 is used as the point of reference. In other embodiments, other types of tissue may be used as reference. In some embodiments, the system 10 includes a user-interface that allows a user to select the type of tissue for use as reference, and the processor 54 will automatically adjust the image contrast based on the input and variability in HU statistics. In the illustrated embodiments, the adjustment of the contrast-enhanced image may be performed by the processor 54. In some embodiments, the system 10 includes a user interface for allowing a user to input HU threshold(s) (e.g., for brightness adjustment) or prescribed range(s) (e.g., for contrast adjustment) of HU to thereby identify possible suspects of cancerous tissue. In other embodiments, the contrast-enhanced image may already have a characteristic that allows target(s), e.g., possible suspect(s) of cancerous cells, to be identified in the contrast-enhanced image. In such cases, there is no need to adjust the contrast and brightness of the contrast-enhanced image, and the method 200 does not include step 204.

Returning to FIG. 2, a non-contrast-enhanced image is next obtained (Step 206). In the illustrated embodiments, the act of obtaining the non-contrast-enhanced image is performed during a treatment session. For example, the same imaging system 10 (which may be located next to a treatment machine), or another system with imaging capability (such as a treatment machine with an imaging source) may be used to create the non-contrast-enhanced image. This may be performed before a delivery of a treatment beam to determine and/or verify a position of a target. When using the imaging system 10 to obtain the non-contrast-enhanced image, the x-ray source assembly 20 projects a beam 26 of x-rays towards the detector assembly 24 on an opposite side of the gantry 12, while the gantry 12 rotates about the portion in the patient 16. In the illustrated embodiments, the patient 16 should be positioned such that the imaging device can image a portion of the patient 16 that contains the target(s) identified in step 204. As the gantry 12 rotates, the detector assembly 24 generates projection images at different gantry angles. In some cases, a number of projection images may be used in a reconstruction process to create a three-dimensional image (CT image). For the purpose of step 206, the non-contrast-enhanced image may be any of the projection images, the CT image itself, or any part of the CT image (such as a two-dimensional slice). In the illustrated embodiments, the act of obtaining the non-contrast-enhanced image is performed by the processor 54 receiving the non-contrast-enhanced image, e.g., from the detector assembly 24 or another medium that stores the non-contrast-enhanced image. In some embodiments, the act of obtaining the non-contrast-enhanced image may also include the act of creating the non-contrast-enhanced image, as described herein.

Figure 5:
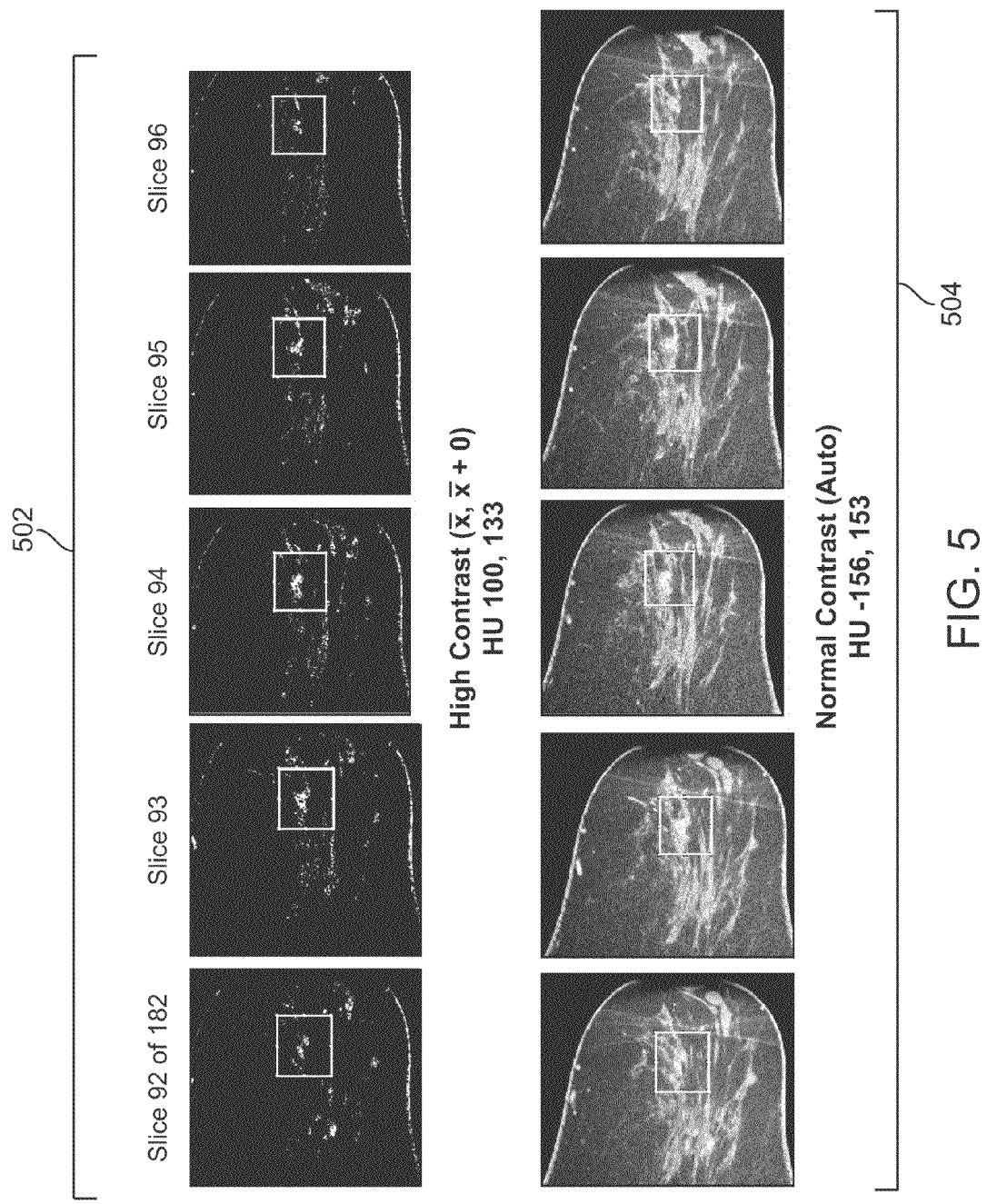
FIG. 5 illustrates contrast-enhanced images having image contrast adjusted in accordance with different criteria in accordance with some embodiments.

Next, the contrast-enhanced image is adjusted in brightness and/or contrast so that an object in the adjusted contrast-enhanced image can also be identified in an appropriately adjusted non-contrast-enhanced image (Step 208). In the illustrated embodiments, the contrast-enhanced image is adjusted such that objects having HU that are above a certain prescribed level (i.e. brightness) and range (i.e. contrast) are visible in the adjusted contrast-enhanced image. For example, the contrast-enhanced image may be adjusted such that all objects having HU that are between −160 and 160 are visible in the contrast-enhanced image. Unlike the technique described with reference to step 204, in which object(s) with a more limited range of HU is displayed (e.g., for the purpose of identifying possible cancerous tissue), adjusting an image to display objects that have a wider range of HU has the benefit of allowing the contrast-enhanced image to resolve more of the structures with an object for better correlation with similar structures in the adjusted non-contrast-enhanced image. FIG. 5 illustrates this concept. In the figure, two sets of contrast-enhanced images 502, 504 are shown, with the top set 502 having an image contrast adjusted to high contrast (i.e., corresponding to a relatively narrower HU range) for identifying possible target(s), e.g., cancerous tissue, (as described with reference to step 204), and the bottom set 504 having an image contrast adjusted to lower or normal contrast (i.e., corresponding to a relatively wider HU range) to display additional objects in the image, such as healthy tissue, for comparison with the adjusted non-contrast-enhanced image (Step 208). Each pair of the top-and-bottom images is from a same contrast-enhanced image CT data set of a same region in the patient 16, with the contrast in the image in the top set 502 adjusted to display all objects that have HU between 100 and 133, and the contrast in the image in the bottom set 504 adjusted to display all objects that have HU between −156 and 153. Different images in the same set are taken from the same imaging angle, but for different depth of a region that is being imaged. As shown in the bottom set 504 of images in the figure, by displaying all objects with HU that is between −156 and 153, the contrast-enhanced image looks similar to an adjusted non-contrast-enhanced image, such as the example shown in FIG. 3B. This allows an object, such as a glandular region in the contrast-enhanced image to be identified in the non-contrast-enhanced image. In some embodiments, the system 10 may include a user interface that allows a user to prescribe the level (i.e. brightness) and range (i.e. contrast) of HU for displaying certain object(s) in the adjusted contrast-enhanced image.

It should be noted that the contrast-enhanced image does not need to be adjusted based on the example of HU range described above, and that other prescribed ranges of HU may be used in other embodiments, as long as the adjusted contrast-enhanced image has sufficient similarity with the adjusted non-contrast-enhanced image such that object(s) in the contrast-enhanced image can be identified with object(s) in the non-contrast-enhanced image. Thus, two images are considered to have sufficient similarity when a feature (e.g., an object) in one image can be identified in the other image. In other embodiments, the contrast-enhanced image may already have a characteristic that allows it to be compared with the non-contrast-enhanced image to identify common features. In such cases, there is no need to adjust the contrast-enhanced image, and the method 200 does not include step 208.

Returning to method 200, after the image contrast of the contrast-enhanced image has been adjusted, the contrast-enhanced image is compared with the non-contrast-enhanced image to determine the position of the target (Step 210). In some embodiments, from the contrast-enhanced image, the spatial relationship between an identified target (e.g., a cancerous tissue) and an adjacent structure (e.g., healthy tissue, or another cancerous tissue) is determined. For example, the spatial relationship may be an amount of offset between a target and an adjacent structure. Then in step 210, the contrast-enhanced image and the non-contrast-enhanced image are compared to identify the same structure in the non-contrast-enhanced image. Once the same structure in the non-contrast-enhanced image has been identified, the position of the target in the non-contrast-enhanced image may be determined based on the spatial relationship between the target and the structure. For example, the position of the target in the non-contrast-enhanced image may be determined using the same amount of offset between the target and the adjacent structure in the contrast-enhanced image. This technique is beneficial because the target (which may be IDC) in the non-contrast-enhanced image may not be easily discernable from its surrounding structure(s) due to the fact that the image contrast for IDC is similar to that for healthy tissue (e.g., surrounding structures), and/or that the cancer lesion may be embedded inside a glandular tissue region. By identifying a structure in the non-contrast-enhanced image that is the same as that in the contrast-enhanced image, and by knowing the spatial relationship between the structure and the target, a location at which the target should be located in the non-contrast-enhanced image may be determined.

Various techniques may be used to compare the contrast-enhanced image with the non-contrast-enhanced image to identify objects that are common in both images. In the illustrated embodiments, the processor 54 may be configured (e.g., programmed and/or built) to perform cross-correlation between the contrast-enhanced image (or a subset of the contrast-enhanced image, e.g., a ROI that contains a target) and the non-contrast-enhanced image (or a subset of the non-contrast-enhanced image). In other embodiments, the comparison of the contrast-enhanced image with the non-contrast-enhanced image may be performed manually by a user.

After the position of a target in the non-contrast-enhanced image has been determined, the processor 54 may use such information to determine the position of the target relative to certain coordinate system, such as the coordinate system of a machine, e.g., a treatment machine or an imaging machine. The act of determining the position of the target relative to the coordinate system may be performed in real time such that the determined position is substantially the same (e.g., within ±2 mm for the case when the target is a moving target) as the actual position of the target. In some cases, the act of determining the position of the target may be considered to be performed in real time if the processor 54 determines the position within 2 seconds since the non-contrast-enhanced image is generated. In such cases, the determined position would be considered to be substantially the same as the actual position of the target. In some embodiments, a set of contrast-enhanced images taken from a same imaging angle, but for different depths of an imaged region is provided (such as those in the bottom set 504 shown in FIG. 5). This may be accomplished by determining different image slices from a three-dimensional contrast-enhanced image. The position of the imaged region relative to a machine coordinate is also determined when the set of contrast-enhanced images are generated. Then in step 210, for each non-contrast image, the processor 54 determines one of the contrast-enhanced images from the set that best matches the non-contrast image. For example, the processor 54 may be configured to determine a cross-correlation between the non-contrast-enhanced image with each one in the set of the contrast-enhanced images. The processor 54 then selects the contrast-enhanced image with the highest cross-correlation value to be the match. After a match has been found, the processor 54 then determines a relative shift of an image of an object between the contrast-enhanced image and the non-contrast-enhanced image, and uses such information to determine a two dimensional coordinate (x, y) for the target. For example, the processor 54 may register a point relative to a coordinate of the machine that is used to generate the contrast-enhanced image, with a point relative to a coordinate of the machine (which may or may not be the same machine for generating the contrast-enhanced image) that is used to generate the non-contrast-enhanced image. Based on this registration, and the determined shift of an object as it appears in the contrast-enhanced image and the non-contrast-enhanced image, the processor 54 can then determine the a two dimensional coordinate for the target. The processor 54 also uses the depth information that corresponds to the slice image with the matched similarity to determine a coordinate in the third dimension (z) for the target. As a result, a three-dimensional coordinate (x, y, z) is determined for the target.

Other techniques may also be used to determine a three-dimensional coordinate of a target. For example, in other embodiments, different contrast-enhanced images that correspond to different gantry angles may be obtained in step 202. In such cases, the processor 54 may obtain two non-contrast-enhanced images in step 206. The processor 54 then determines two contrast-enhanced images from the set that best match the corresponding two non-contrast-enhanced images. The first match provides a first two-dimensional coordinate for a target, and the second match provides a second two-dimensional coordinate for a target. The two two-dimensional coordinates may then be triangulated to obtain a three-dimensional coordinate for the target.

In the above embodiments, the method 200 has been described as being performed to verify or determine a target position during a treatment session (e.g., before a delivery of a radiation beam, or between delivery of beams in the same session, as in a fractionated radiation therapy). Alternatively, or additionally, the method 200 may be performed during a radiation delivery session to track a position of the target. For example, in some embodiments, the step 206 may be repeated to obtain non-contrast-enhanced images of the patient 16 as the patient 16 undergoes movement. For each non-contrast-enhanced image, step 210 may be performed in real time to determine the corresponding position of the target. By repeating step 210 for different non-contrast-enhanced images as they are generated in a sequence, the target may be tracked. In some embodiments, the tracked positions may be used to control a treatment machine that is used to treat the patient 16. For example, the processor 54 may be configured for turning on a radiation beam, turning off a radiation beam, moving one or more leaves of a collimator, positioning a collimator, moving a radiation source, rotating a gantry, moving a patient support, changing an energy level of a radiation beam, or any combination of the foregoing, based on one or more determined positions of the target.

As illustrated in the above embodiments, the method 200 uses matching of structural patterns, around or adjacent a suspected or known cancer mass, to provide precise localizations. This is advantageous in that it allows cancer lesion (which is otherwise impossible or very difficult to identify using only non-contrast-enhanced image) that is embedded inside glandular tissue region to be localized for treatment. The above technique is also advantageous in that it does not require a contrast agent to be delivered for each treatment session in order to accurately achieve tumor targeting. Radio therapy may involve daily targeting and radiation treatment delivery, five or more days per week, and spanning a total 4 to 6 weeks. Use of the above technique greatly reduces the number of times such contrast must be injected for precise tumor targeting. In some cases, only one contrast injection needs to be performed, and the contrast-enhanced image(s) may be used for the whole radiation therapy process, which in some cases, may span a couple of weeks. If desired, contrast agent could be injected, say weekly, to assist in this process, particularly when one wants to track the response of the cancer mass to treatment delivery. In this case, the number of times that the contrast agent is injected is still less than the number of times for the case in which contrast agent is injected in every treatment session for the entire radiation therapy process. The above technique is also advantageous because it allows reliable identification and localization of a presence of cancer lesion masses with smaller volumes. Detection of smaller lesions allows earlier detection of cancer, which in turn, may lead to increased probability of a successful cancer treatment.

In some cases, contrast-enhanced image(s) in the above technique may be used to also identify the extent (e.g., shape and/or size) of lesions in non-contrast-enhanced image(s). For example, at every other treatment session, contrast-enhanced image may be obtained to determine the shape and/or size of lesions. In some cases, if the shape and/or size of the lesion that is desired to be treated has changed (e.g., the lesion may shrink due to previous treatment sessions), the treatment may be adjusted accordingly. This has the benefit of greatly reducing the current margins (into healthy non-malignant tissues) used around known lesions. This has two significant implications. First, the reduction in margins reduces the radiation dose to healthy tissues and thus greatly reduces the morbidity (collateral damage) to the healthy tissue. Second, it allows the dose to be safely escalated to higher doses to the lesion itself. This in turn, increases the chance of complete destruction of the lesion to greatly reduce probability of local recurrence.

In other embodiments, template matching may be used to track target (e.g., cancer lesion). In such cases, a template is formed from one image set (contrast-enhanced image set) and is used to 1) spatially localize the lesion in another image set (non-contrast-enhanced image set), and 2) to extract parameters that represent any size and position changes between the sets. The changes from one image set to another set may be due to lesion size and position changes. Therefore template matching needs to be repeated using different spatial scaling of the template. This allows searching not only for the best location match but also for the best size match. In some embodiments, the scaling parameter resulting in the best match may represent the size change. Depending on the granularity of the scale parameters used, interpolation around the best matching scale parameter can be used to obtain a more accurate estimate of the size and position changes. For example, whenever one searches over a discrete set of values of a parameter for best match, interpolating the parameter values around the best match value will give more accurate value of the optimum parameter. This is analogous to finding the position of the maximum of a function of a discrete variable. In some embodiments, a similarity measure for template matching may use normalized cross correlation because changes of contrast and intensity between the two image sets are expected while the shape (but not size) may be somewhat invariant. For example, the following cross correlation function may be used in some embodiments:

$$C_n(dx, dy, dz) = \sum\sum (T(x, y, z, s) - m_T)$$
$$(I(x - dx, y - dy, z - dz) - m_{dx,dy,dz}) / (\sigma_T \sigma_{dx,dy,dz})$$

where $T(x,y,z,s)$ is the template spatially scaled by the parameter s. The variables $dx,dy,dz$ represent the spatial search parameters. In such cases, normalization to intensity mean values $m_T$ and $m_{dx,dy,dz}$, and standard deviations $\sigma_T \sigma_{dx,dy,dz}$ allow changes in the contrast and background levels without affecting similarity match based on shape.

In some cases, spatial filtering of the two images before this template matching may be performed. The purpose of filtering is 1) to reduce noise (e.g., using a low-pass spatial filter), and 2) to remove local intensity variations (e.g., using a high-pass spatial filter) within the lesion volume that can be inconsistent from image to image and result in a reduced value of similarity measure. The spatial filter may be implemented as a form of bandpass filter with appropriate cut-off frequencies that while reducing noise, preserve matching features, and remove intensity variations within the lesion volume. In some cases, the templates may be modified to have certain exclusion areas, so that the actual suspect lesion ROI may be excluded from the matching process. In such cases, each template may be an image with "holes", and/or an image formed by different image portions that may or may not be connected to each other. This allows only the surrounding areas to be used in the matching process and eliminates the use of the enhanced ROI for the suspect lesion. This is because the shift (i.e., between the position matches of contrast-enhanced and non-contrast-enhanced 3D CT data sets from comparative analysis of 2D slice images produced from them) due to the ROI with the suspect lesion may be much larger than the relatively more uniform shifts for the remainder of the image set provided by contrast enhancement. In other embodiments, mutual information may be used as a similarity measure. Here is the equation:

$$I(X;Y) = \sum_{y \in Y}\sum_{x \in X} p(x, y)\log\left(\frac{p(x, y)}{p_1(x)p_2(y)}\right),$$

where $p(x,y)$ is the joint intensity histogram of the two image pieces $T(x,y,z,s)$ and $I(x-dx,y-dy-z-dz)$ using the notation in cross correlation above, and $p1(x)$ and $p2(x)$ are individual intensity histograms of the these image pieces. So a different value of $I(X,Y)$ results with every value of the shift vector $(dx, dy, dz)$ and scale s. Maximum mutual information corresponds to the matching shift and scale parameters. This similarity measure is particularly useful when there are random contrast reversals such as those encountered when matching images created from two different modalities (e.g., imaging techniques, e.g., MR vs. CT). Contrast reversal can result when two different images of the same object taken under different conditions and/or modalities preserve the "spatial pattern" of the object, but the intensity of different areas of the image can change, sometimes randomly. In some cases, a specific boundary position is preserved between different modalities, but the intensity values on the two sides of the boundary change to the extent that the contrast has been reversed. Mutual information is a good similarity measure when spatial patterns are preserved while intensities change between the two images. In some cases, cross correlation may not be a good similarity measure because random intensity changes can reduce its average value to zero. In some embodiments, when the two images that are being matched are from the same imaging modality (e.g., x-ray modality), use of normalized cross correlation is sufficient, and is desirable because it is much less computationally demanding.

Figure 6:
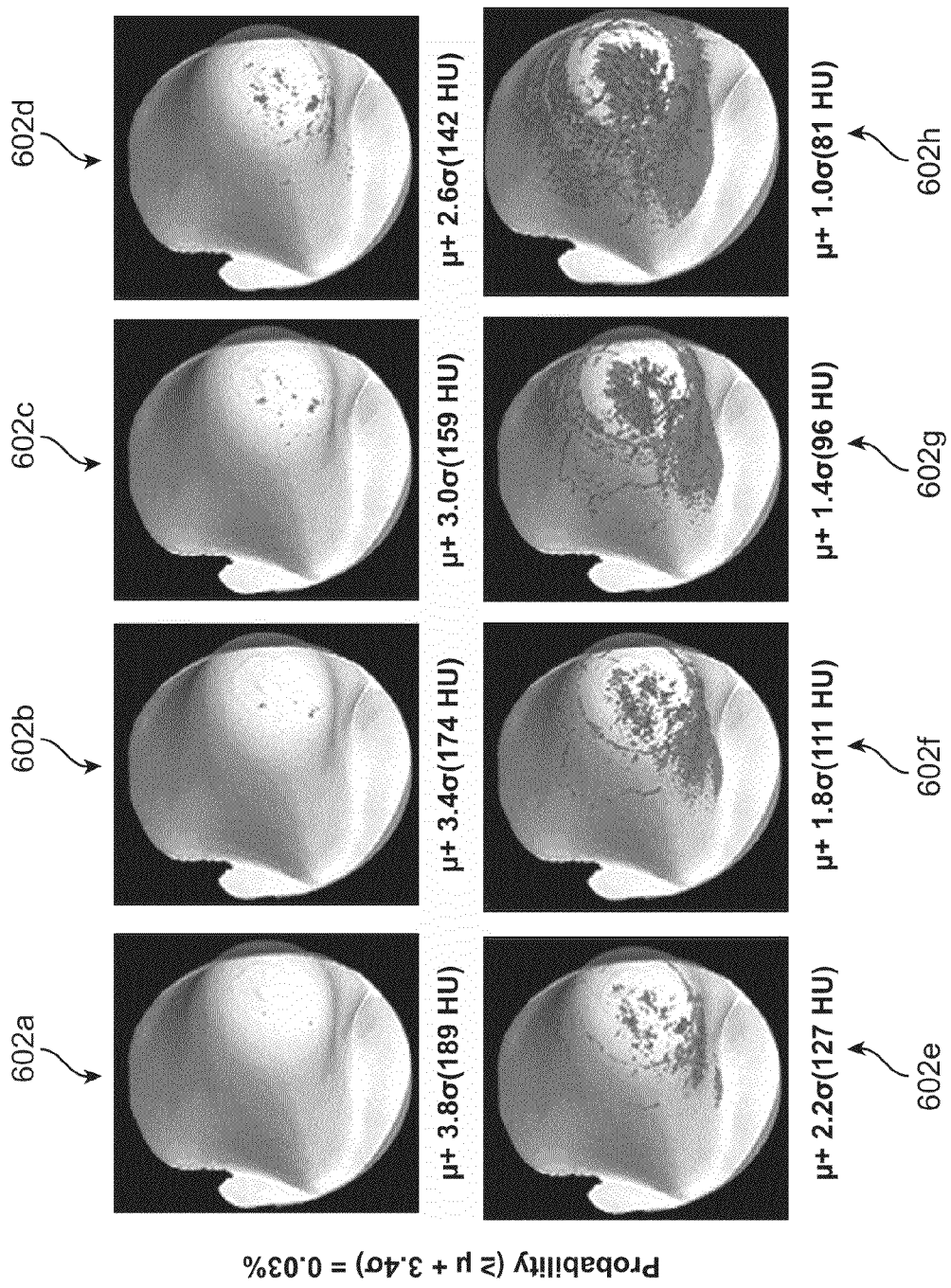
FIG. 6 illustrates a surface rendering technique to identify possible suspect(s) of cancer lesion in accordance with some embodiments.

In any of the embodiments described herein, surface rendering and HU statistics may be used to identify suspect cancer ROIs (examples of "target") from the adjusted contrast-enhanced image (e.g., cone beam CT or digital tomosynthesis data sets). Such may be performed, for example, in step 204 of method 200. Surface rendering presents 3D perspective images of regions whose surfaces all have the same (contrast enhanced) HU value. FIG. 6 illustrates several images 602a-602h created from a set of contrast-enhanced images (that are used to obtain the ones shown in FIG. 5) by surface rendering and converting them into 3D perspective views of the whole CT data set. Starting in the upper left side of FIG. 6 and going right and then down, the HU value used to define these 3D surfaces is constantly decreased (i.e., from images 602a-602h). When it was set at 189 HU (upper left), essentially no regions in the breast had HU values that high. When it was lowered to 174 HU (image 602b), about 3 or 4 regions were "rendered" with HU values that high. Since high HU value is correlated with iodine leakage and the presence of cancer, these first regions to appear have high probability of being cancer lesions. If the rendering criterion is lowered to 159 HU (image 602c), perhaps 10 or more "contrast enhanced" and "suspect cancer ROI's" are visualized. In the image 602c for 159 HU, two larger foci on the lower right hand side of the µ+3.0σ plot are shown. In some embodiments, this may be as low as someone may choose to go with rendering an image data set to identify suspect cancer lesion positions and sizes. As one lowers this criterion level further, more of the whole anatomy inside the breast will be included in the image, and such additional anatomy that appears with the lowering of the criterion has much lower probability of being malignant cancer. These criterion HU values are also shown in terms of mean and standard deviation values (mu µ and sigma σ) of healthy glandular breast tissue, which may be more helpful to use when trying to compare one patient with another one.

In the images of FIG. 6, skin surface is displayed in white and was chosen to be the surface with a HU value of −350 HU. Since free space has an HU value of −1000 HU, this −350 HU criterion conveniently selects the surface just outside the skin. The red rendered surfaces in the figure are created by selecting a criterion that varies from 81 HU up to 189 HU, corresponding respectively to the mean (µ=49.6 HU) of the glandular tissue plus from 1.0 to 3.8 times the standard deviation (σ=33.8 HU) of the glandular tissue. All of these red surfaces surround regions containing voxels of the criterion value or higher. From the statistics of normal distributions, there is an established probability that a ROI with the criterion value, could have come from a normal (not malignant) glandular distribution, of the specified mean µ and standard deviation σ. For the value of µ+3.4σ (image 602b) this probability is 0.034%. Hence, it is very likely that the red ROIs, with voxels having HU values equal to or exceeding μ+3.4σ could have come from healthy glandular tissue. In the illustrated embodiments, the probabilities of a certain region coming from a normal distribution are 16%, 8.1%, 3.6%, 1.4%, 0.47%, 0.14% and 0.0072% respectively for the μ plus 1.0σ, 1.4σ, 1.8σ, 2.2σ, 2.6σ, 3.0σ and 3.8σ criterion values. In some cases, little or no breast cancer masses originate from the adipose or fat regions of the breast, and the HU values of the skin are typically higher than that of glandular tissue. Hence, in some embodiments, highlighting regions that are statistically well above most of the glandular values, constitutes a useful way of determining regions of possible malignancy. As seen in FIG. 6, as the criterion for the red surface is raised (i.e., going from images 602h to 602a), the red surface rendered regions begin to separate into distinct volumes, which become more compactly defined, until at the highest criterion values, all the regions begin to disappear. It is these distinct and well defined regions, which are most unlikely to have originated (by chance) from normal glandular distributions and are thus highly suspicious of being malignant. Some of these distinct volumes are quite small, with diameters approaching 1 mm in size. In some embodiments, this can be used as the first step in identifying which regions (even small ones embedded in regular glandular tissue) can be used for matching with similar regions in corresponding data sets (i.e., non-contrast-enhanced image(s) with no contrast enhancement).

Figure 7:
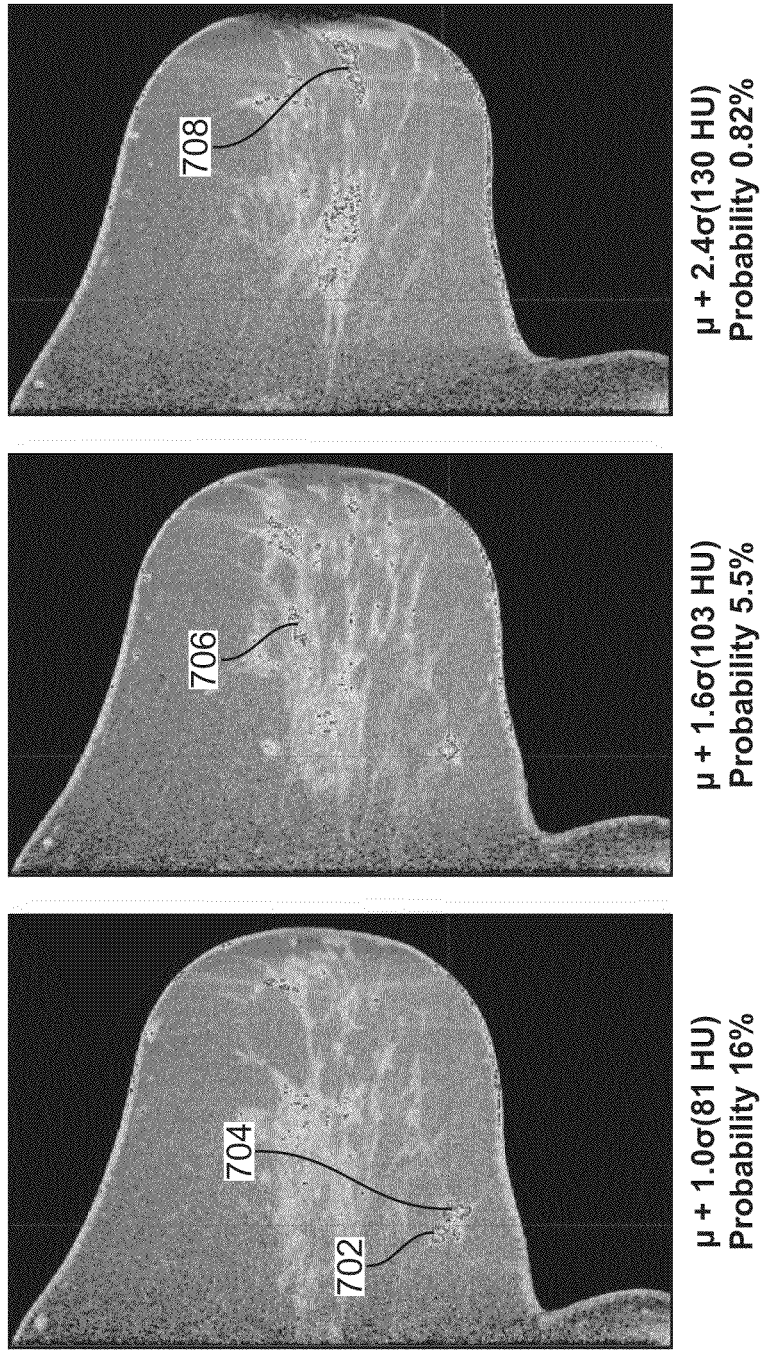
FIG. 7 illustrates multiple contrast-enhanced images superimposed with contour lines of constant image intensity or HU values in accordance with some embodiments.

Also, in any of the embodiments described herein, the contrast-enhanced image (with a first adjusted image brightness and contrast) may be superimposed with the same contrast-enhanced image (with a second adjusted image contrast), and objects with different HU values may be selectively displayed (e.g., by prescribing HU threshold(s) using a user interface) to determine different probabilities that a certain region has cancerous tissue. Such may be performed, for example, in step 204 of method 200 in order to identify possible suspect(s) of cancerous tissue, and/or in step 208. FIG. 7 illustrates three sequentially deeper slices (sequential in space (depth)) from an iodine contrast enhanced data set. In the figure, the green contours correspond to the locus of adjacent points that all have an HU value of 81, which corresponds to a probability of 16% (i.e., 16% chance that the regions are from normal glandular tissue). The blue and magenta contours are the locus of adjacent points that all have HU values of 103 and 130 respectively, with respective probabilities of 5.5% and 0.82%. Since these are superimposed on image slices with normal contrast—i.e., the second adjusted image contrast and brightness (so that the whole range of gray scale values are displayed), the actual features and their various probabilities can be viewed simultaneously. The two (magenta) foci 702, 704 of the IDC are evident in lower portion of the left and middle plots of FIG. 7. Another region 706 is shown as the magenta spot in the center portion of the middle plot of FIG. 7. An additional magenta-colored spot 708 can be seen at the center right portion of the right plot of FIG. 7, plus some possible skin involvement in the bottom part of the right plot. After the possible suspect(s) of cancerous tissue has been identified, the position(s) of the target(s) can be determined using structural matching technique without injection of contrast, as described herein. In other embodiments, instead of superimposing the contrast-enhanced images with different adjusted image contrasts, a first contrast-enhanced image (displaying objects with a prescribed range of HU values) may be superimposed with a non-contrast-enhanced image (displaying objects with wider range of HU values), as described herein.

It should be noted that the method 200 needs not be performed using a CT imaging system. In other embodiments, instead of using a CT imaging system to perform the functions described herein, other imaging systems may also be used. For example, in other embodiments, a digital tomosynthesis system (in which case, the contrast-enhanced images would be tomosynthesis images), or an x-ray imaging system may be used. Also, in further embodiments, the technique described herein may be used to monitor a response of a lesion to treatments, including chemo or gene therapies, or any other cancer therapies and treatments. Further, it should be noted that the steps in method 200 need not be performed in the order shown, and that in other embodiments, the steps may be performed in other orders.

Computer System Architecture

Figure 8:
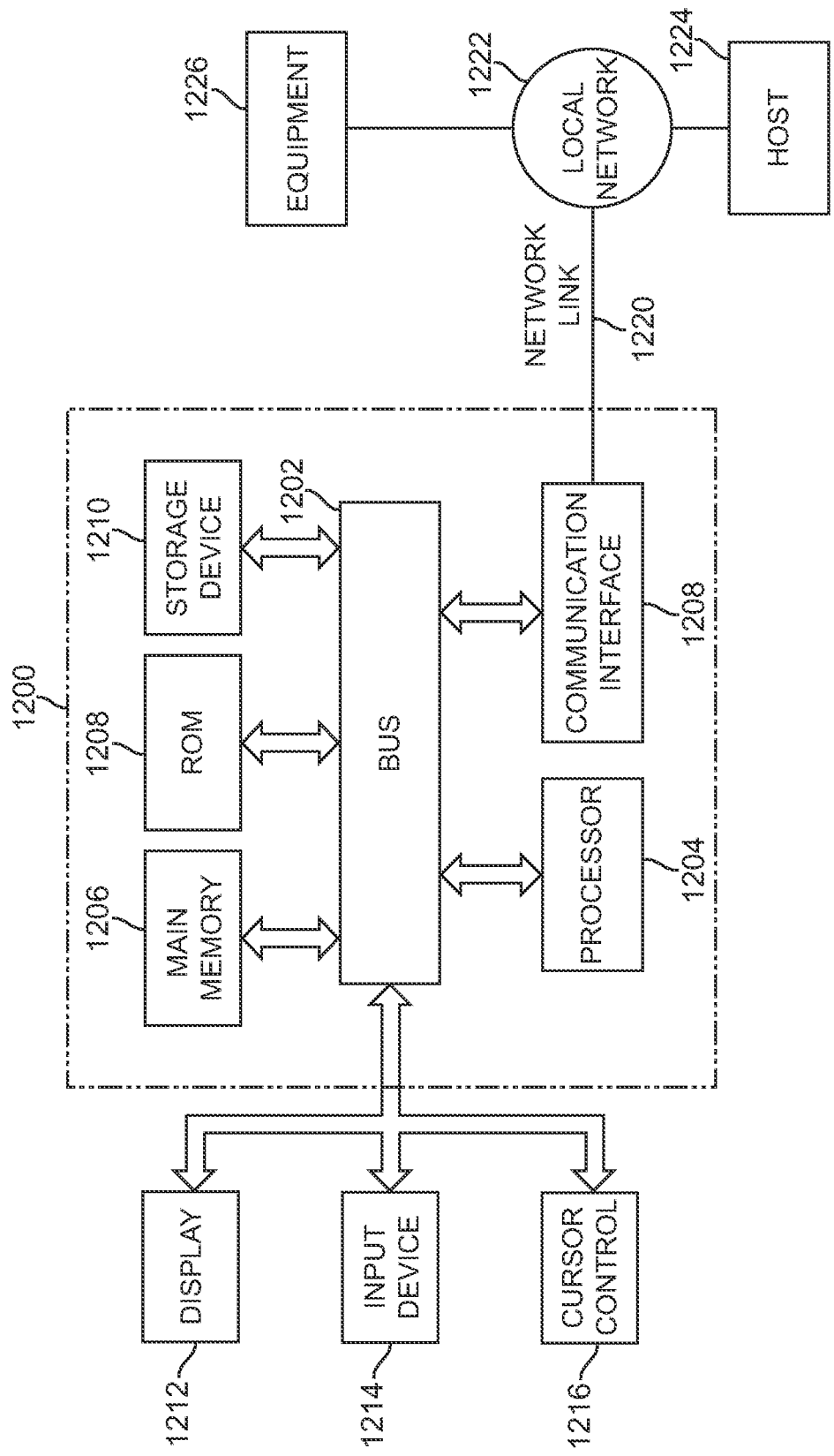
FIG. 8 is a block diagram of a computer system architecture, with which embodiments described herein may be implemented.

FIG. 8 is a block diagram that illustrates an embodiment of a computer system 1200 upon which an embodiment of the invention may be implemented. Computer system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. In some cases, the computer system 1200 may be used to implement the processor 54. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT) or a flat panel, for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention.

Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. Volatile media includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network (s), the network link 1220, and the communication interface 1218.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, the term "image" needs not be limited to an image that is displayed visually, and may refer to image data that is stored. In addition, the term "image" may refer to an entire image frame itself, or to a part of an image frame. Thus, the term "image" may refer to an image portion. Also, the term "processor" may include one or more processing units, and may refer to any device that is capable of performing mathematical computation implemented using hardware and/or software. Further, in any of the embodiments described herein, instead of using the processor 54 to perform the various functions described, a separate processor may be used. In addition, the term "object" may refer to any anatomical structure, such as healthy tissue or abnormal tissue. It should also be noted that the term "target" is not limited to an object in a body that is desired to be treated, and that it may refer to any object (such as healthy tissue, abnormal tissue, or a marker), or it may refer to a track point that may or may not be on a particular object. For example, in other embodiments, the term "target" may refer to a point that is desired to be tracked, wherein the point may be a center-of-mass of two or more markers. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method for determining a tissue position in a medical procedure, comprising:
    obtaining a contrast-enhanced image of a portion of a patient, the portion of the patient comprising tissue;
    obtaining a non-contrast-enhanced image of the portion, wherein the contrast-enhanced image and the non-contrast-enhanced image are created at different times; and
    determining a position of the tissue using the contrast-enhanced image and the non-contrast-enhanced image, wherein the position is determined using a processor that is configured for comparing the contrast-enhanced image with the non-contrast-enhanced image to identify an object that is common in both the contrast-enhanced image and the non-contrast-enhanced image, and using the identified object to determine the position of the tissue.

2. The method of claim 1, wherein the act of determining the position is performed in real time so that the determined position is substantially the same as an actual position of the tissue.

3. The method of claim 1, wherein the act of determining the position is performed during a treatment session.

4. The method of claim 3, wherein the act of determining the position is performed before a delivery of a radiation treatment beam.

5. The method of claim 3, wherein the act of determining the position is performed between deliveries of radiation treatment beams.

6. The method of claim 1, further comprising:
    obtaining additional non-contrast-enhanced images; and determining additional positions of the tissue using the additional non-contrast-enhanced images as the tissue undergoes motion, thereby tracking the tissue.

7. The method of claim 1, wherein the tissue is not discernable from its surrounding structure in the non-contrast-enhanced image.

8. The method of claim 1, further comprising adjusting one or both of a contrast and a brightness of the contrast-enhanced image such that only target(s) including the tissue that is suspect of an abnormal tissue is visible in the adjusted contrast-enhanced image.

9. The method of claim 1, further comprising adjusting one or both of a contrast and a brightness of the contrast-enhanced image such that structures in the portion having corresponding HU that are below HU=100 are not visible in the adjusted contrast-enhanced image.

10. The method of claim 1, further comprising adjusting one or both of a contrast and a brightness of the contrast-enhanced image such that the adjusted contrast-enhanced image looks similar to the non-contrast-enhanced image.

11. The method of claim 1, further comprising adjusting one or both of a contrast and a brightness of the contrast-enhanced image such that structures in the portion having corresponding HU that are below HU=100 are visible in the contrast-enhanced image.

12. The method of claim 1, wherein the tissue is a part of the object.

13. The method of claim 1, further comprising:
adjusting one or both of a contrast and brightness of the contrast-enhanced image a first time such that only target(s) including the tissue that is a suspect of abnormal tissue is visible in the contrast-enhanced image; and
adjusting one or both of the contrast and the brightness of the contrast-enhanced image a second time such that the object in the contrast-enhanced image looks similar to the object as it appears in the non-contrast-enhanced image, wherein the tissue is a part of, or adjacent to, the object.

14. The method of claim 1, wherein the tissue comprises cancerous tissue.

15. The method of claim 1, wherein the tissue comprises healthy tissue.

16. The method of claim 1, further comprising using the determined position to control a treatment machine.

17. The method of claim 16, wherein the act of controlling the treatment machine comprises turning on a radiation treatment beam, turning off a radiation treatment beam, moving one or more leaves of a collimator, positioning a collimator, moving a radiation source, rotating a gantry, moving a patient support, or changing an energy level of a radiation treatment beam.

18. The method of claim 1, wherein the act of obtaining the contrast-enhanced image comprises using the processor to receive the contrast-enhanced image.

19. The method of claim 1, further comprising generating the contrast-enhanced image, wherein the act of generating the contrast-enhanced image comprises using a radiation machine to generate a plurality of projection images of the portion of the patient at different gantry angles.

20. The method of claim 19, wherein the radiation machine comprises a CT machine.

21. The method of claim 1, wherein the position of the tissue is determined relative to a coordinate system of a device that is configured for use in a treatment procedure.

22. The method of claim 1, wherein the tissue is adjacent to the object.

23. The method of claim 1, wherein the object comprises an anatomical structure that is different from the tissue.

24. A system for use in a medical procedure, comprising:
a processor; and
a non-transitory medium storing a set of instructions for execution by the processor to configure the processor for;
obtaining a contrast-enhanced image of a portion of a patient, the portion of the patient comprising tissue;
obtaining a non-contrast-enhanced image of the portion, wherein the contrast-enhanced image and the non-contrast-enhanced image are created at different times; and
determining a position of the tissue using the contrast-enhanced image and the non-contrast-enhanced image; and
wherein the processor is configured for determining the position of the tissue by comparing the contrast-enhanced image with the non-contrast-enhanced image to identify an object that is common in both the contrast-enhanced image and the non-contrast-enhanced image, and using the identified object to determine the position of the tissue.

25. The system of claim 24, wherein the processor is configured to determine in real time so that the determined position is substantially the same as an actual position of the tissue.

26. The system of claim 24, wherein the processor is configured for:
obtaining additional non-contrast-enhanced images; and
determining additional positions of the tissue using the additional non-contrast-enhanced images as the tissue undergoes motion, thereby tracking the tissue.

27. The system of claim 24, wherein the processor is further configured for adjusting one or both of a contrast and a brightness of the contrast-enhanced image such that only target(s) including the tissue that is suspect of an abnormal tissue is visible in the adjusted contrast-enhanced image.

28. The system of claim 24, wherein the processor is further configured for adjusting one or both of a contrast and a brightness of the contrast-enhanced image such that the contrast-enhanced image looks similar to the non-contrast-enhanced image.

29. The system of claim 24, wherein the tissue is a part of the object.

30. The system of claim 24, wherein the processor is further configured for:
adjusting one or both of a contrast and a brightness of the contrast-enhanced image a first time such that only target(s) including the tissue that is a suspect of abnormal tissue is visible in the adjusted contrast-enhanced image; and
adjusting one or both of the contrast and the brightness of the contrast-enhanced image a second time such that the object in the contrast-enhanced image looks similar to the object as it appears in the non-contrast-enhanced image, wherein the tissue is a part of, or adjacent to, the object.

31. The system of claim 24, wherein the processor is further configured for using the determined position to control a treatment machine.

32. The system of claim 31, wherein the processor is configured for controlling the treatment machine by turning on a radiation treatment beam, turning off a radiation treatment beam, moving one or more leaves of a collimator, positioning a collimator, moving a radiation source, rotating a gantry, moving a patient support, or changing an energy level of a radiation treatment beam.

33. The system of claim 24, wherein the processor is configured to determine the position of the tissue relative to a coordinate system of a device that is configured for use in a treatment procedure.

34. The system of claim 24, wherein the tissue is adjacent to the object.

35. The system of claim 24, wherein the object comprises an anatomical structure that is different from the tissue.

36. A method for use determining a tissue position in a medical procedure, comprising:
obtaining a contrast-enhanced image of a portion of a patient, the portion of the patient comprising tissue;
obtaining a non-contrast-enhanced image of the portion; and
determining a position of the tissue using the contrast-enhanced image and the non-contrast-enhanced image, wherein the position is determined using a processor that is configured for comparing the contrast-enhanced image with the non-contrast-enhanced image to identify an object that is common in both the contrast-enhanced image and the non-contrast-enhanced image, and using the identified object to determine the position of the tissue;
wherein the act of determining the position is performed in substantially real time.

37. The method of claim 36, wherein the act of determining the position is performed in real time so that the determined position is substantially the same as an actual position of the tissue.

38. The method of claim 36, wherein the act of determining the position is performed during a treatment session.

39. The method of claim 38, wherein the act of determining the position is performed before a delivery of a radiation treatment beam.

40. The method of claim 38, wherein the act of determining the position is performed between deliveries of radiation treatment beams.

41. The method of claim 36, further comprising:
obtaining additional non-contrast-enhanced images; and
determining additional positions of the tissue using the additional non-contrast-enhanced images as the tissue undergoes motion, thereby tracking the tissue.

42. The method of claim 36, wherein the tissue is not discernable from its surrounding structure in the non-contrast-enhanced image.

43. The method of claim 36, further comprising adjusting one or both of a contrast and a brightness of the contrast-enhanced image such that only target(s) including the tissue that is suspect of an abnormal tissue is visible in the adjusted contrast-enhanced image.

44. The method of claim 36, further comprising adjusting one or both of a contrast and a brightness of the contrast-enhanced image such that the adjusted contrast-enhanced image looks similar to the non-contrast-enhanced image.

45. The method of claim 36, wherein the tissue is a part of the object.

46. The method of claim 36, further comprising:
adjusting one or both of a contrast and a brightness of the contrast-enhanced image a first time such that only target(s) including the tissue that is a suspect of abnormal tissue is visible in the adjusted contrast-enhanced image; and
adjusting one or both of the contrast and the brightness of the contrast-enhanced image a second time such that the object in the contrast-enhanced image looks similar to the object as it appears in the non-contrast-enhanced image, wherein the tissue is a part of, or adjacent to, the object.

47. The method of claim 36, further comprising using the determined position to control a treatment machine.

48. The method of claim 47, wherein the act of controlling the treatment machine comprises turning on a radiation treatment beam, turning off a radiation treatment beam, moving one or more leaves of a collimator, positioning a collimator, moving a radiation source, rotating a gantry, moving a patient support, or changing an energy level of a radiation treatment beam.

49. The method of claim 36, wherein the position of the tissue is determined relative to a coordinate system of a device that is configured for use in a treatment procedure.

50. The method of claim 36, wherein the tissue is adjacent to the object.

51. The method of claim 36, wherein the object comprises an anatomical structure that is different from the tissue.

52. A system for use in a medical procedure, comprising:
a processor; and
a non-transitory medium storing a set of instructions for execution by the processor to configure the processor for;
obtaining a contrast-enhanced image of a portion of a patient, the portion of the patient comprising tissue,
obtaining a non-contrast-enhanced image of the portion, and
determining a position of the tissue using the contrast-enhanced image and the non-contrast-enhanced image;
wherein the act of determining the position is performed in substantially real time; and
wherein the processor is configured for determining the position of the tissue by comparing the contrast-enhanced image with the non-contrast-enhanced image to identify an object that is common in both the contrast-enhanced image and the non-contrast-enhanced image, and using the identified object to determine the position of the tissue.

53. The system of claim 52, wherein the processor is configured to determine the position in real time so that the determined position is substantially the same as an actual position of the tissue.

54. The system of claim 52, wherein the processor is configured to determine the position during a treatment session.

55. The system of claim 54, wherein the processor is configured to determine the position before a delivery of a radiation treatment beam.

56. The system of claim 54, wherein the processor is configured to determine the position between deliveries of radiation treatment beams.

57. The system of claim 52, wherein the processor is further configured for:
obtaining additional non-contrast-enhanced images; and
determining additional positions of the tissue using the additional non-contrast-enhanced images as the tissue undergoes motion, thereby tracking the tissue.

58. The system of claim 52, wherein the tissue is not discernable from its surrounding structure in the non-contrast-enhanced image.

59. The system of claim 52, wherein the processor is further configured for adjusting one or both of a contrast and a brightness of the contrast-enhanced image such that only target(s) including the tissue that is suspect of an abnormal tissue is visible in the adjusted contrast-enhanced image.

60. The system of claim 52, wherein the processor is further configured for adjusting one or both of a contrast and a brightness of the contrast-enhanced image such that the adjusted contrast-enhanced image looks similar to the non-contrast-enhanced image.

61. The system of claim 52, wherein the tissue is a part of the object.

62. The system of claim 52, wherein the processor is further configured for:
   adjusting one or both of a contrast and a brightness of the contrast-enhanced image a first time such that only target(s) including the tissue that is a suspect of abnormal tissue is visible in the adjusted contrast-enhanced image; and
   adjusting one or both of the contrast and the brightness of the contrast-enhanced image a second time such that the object in the contrast-enhanced image looks similar to the object as it appears in the non-contrast-enhanced image, wherein the tissue is a part of, or adjacent to, the object.

63. The system of claim 52, wherein the processor is further configured for using the determined position to control a treatment machine.

64. The system of claim 63, wherein the processor is configured for controlling the treatment machine by turning on a radiation treatment beam, turning off a radiation treatment beam, moving one or more leaves of a collimator, positioning a collimator, moving a radiation source, rotating a gantry, moving a patient support, or changing an energy level of a radiation treatment beam.

65. The system of claim 52, wherein the processor is configured for determining the position of the tissue relative to a coordinate system of a device that is configured for use in a treatment procedure.

66. The system of claim 52, wherein the tissue is adjacent to the object.

67. The system of claim 52, wherein the object comprises an anatomical structure that is different from the tissue.

* * * * *

UNITED STATES PATENT AND TRADEMARK OFFICE
CERTIFICATE OF CORRECTION

| | | |
|---|---|---|
| PATENT NO. | : 8,483,803 B2 | Page 1 of 1 |
| APPLICATION NO. | : 12/210813 | |
| DATED | : July 9, 2013 | |
| INVENTOR(S) | : Partain | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1054 days.

Signed and Sealed this
Tenth Day of February, 2015

Michelle K. Lee
*Deputy Director of the United States Patent and Trademark Office*